United States Patent
Barron et al.

(10) Patent No.: US 11,339,111 B2
(45) Date of Patent: May 24, 2022

(54) POLYKETIDE COMPOUND AND DERIVATIVES THEREOF FOR USE IN THE PREVENTION AND TREATMENT OF A NEUROLOGICAL DISORDER

(71) Applicant: SOCIETE DES PRODUITS NESTLE S.A., Vevey (CH)

(72) Inventors: Denis Marcel Barron, Lutry (CH); Olivier Ciclet, Veyrier (CH); Alexandre Grand-Guillaume-Perrenoud, Preverenges (CH); Martine Naranjo Pinta, Morges (CH); Yann Ratinaud, Morges (CH); Jonathan Thevenet, Publier (FR); Andreas Wiederkehr, Blonay (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/767,735

(22) PCT Filed: Nov. 27, 2018

(86) PCT No.: PCT/EP2018/082629
§ 371 (c)(1),
(2) Date: May 28, 2020

(87) PCT Pub. No.: WO2019/105905
PCT Pub. Date: Jun. 6, 2019

(65) Prior Publication Data
US 2020/0361848 A1 Nov. 19, 2020

(30) Foreign Application Priority Data
Nov. 30, 2017 (EP) .................................. 17204659

(51) Int. Cl.
*C07C 59/92* (2006.01)
*C07D 313/00* (2006.01)

(52) U.S. Cl.
CPC ............ *C07C 59/92* (2013.01); *C07D 313/00* (2013.01)

(58) Field of Classification Search
CPC ..................................................... C07C 59/92
See application file for complete search history.

(56) References Cited

FOREIGN PATENT DOCUMENTS

| EP | 0689839 | 1/1996 |
|----|---------|--------|
| WO | 2008104976 | 9/2008 |
| WO | 2011061667 | 5/2011 |
| WO | 2013040206 | 3/2013 |

OTHER PUBLICATIONS

Kane et al. "Inhibitors of V-Type ATPases, Bafilomycin A1 and Concanamycin A, Protect Against Beta-Amyloid-Mediated Effects on 3-(4,5-Dimethylthiazol-2-yl)-2,5-Diphenyltetrazolium Bromide (MTT) Reduction" Journal of Neurochemistry, 1999, vol. 72, pp. 1939-1947.
Oniciu et al. "Long hydrocarbon chain diols and diacids with central ether or ketone moieties that favorably alter lipid disorders" Pharmazie, 2006, vol. 61, pp. 157-165.
Mueller et al. "Long Hydrocarbon Chain Keto Diols and Diacids that Favorably Alter Lipid Disorders in Vivo" Journal of Medicinal Chemistry, 2004, vol. 47, No. 24, pp. 6082-6099.
Ohara et al. "Glucose tolerance status and risk of dementia in the community: The Hisayama Study" Neurology, 2011, vol. 77, No. 12, pp. 1126-1134.

*Primary Examiner* — Golam M Shameem
(74) *Attorney, Agent, or Firm* — K&L Gates LLP

(57) ABSTRACT

The present invention relates to a compound, in particular a polyketide compound and derivatives thereof, for use in the prevention and/or treatment of a neurological disorder in an individual. The compound of the invention can promote lactate secretion. A composition comprising the compound of the invention, and a food or food extract enriched with said compound or composition are also provided.

3 Claims, 16 Drawing Sheets

A.

B.

C.

D.

E.

A.

B.

A.

A.

POLYKETIDE COMPOUND AND DERIVATIVES THEREOF FOR USE IN THE PREVENTION AND TREATMENT OF A NEUROLOGICAL DISORDER

CROSS REFERENCE TO RELATED APPLICATIONS

The present application is a National Stage of International Application No. PCT/EP2018/082629, filed on Nov. 27, 2018, which claims priority to European Patent Application No. 17204659.1, filed on Nov. 30, 2017, the entire contents of which are being incorporated herein by reference.

INTRODUCTION

The brain is an energy demanding organ because many processes linked to neuron and glial cell function require a lot of energy in the form of ATP. In neurons, electrical activity, the restoration of ion gradients across the plasma membrane, as well as synaptic transmission are examples of biological processes that require high levels of energy supply. The brain is therefore strongly dependent on the continuous provision of glucose as neurons do not store glycogen and are unable to oxidize fats as an alternative fuel source.

Glucose metabolism is initiated in the glycolytic pathway that forms ATP, NADH and either of two end-products pyruvate or lactate. In a second step, pyruvate oxidized in the mitochondrial matrix is required to initiate the synthesis of the large majority of ATP molecules to maintain energy homeostasis. The ability of cells of the central nervous system to generate sufficient amounts of energy is essential for brain function. In the aging brain, glucose metabolism is reduced, which may explain declining cognitive function as we get older. Glucose hypometabolism has also been observed in individuals at risk of developing Alzheimer's disease long before clinical symptoms are detected. Interventions improving brain energy metabolism can be used as an approach to prevent cognitive decline during normal aging or neurological diseases.

In addition to glucose, neurons are able to oxidize other fuels such as amino acids (mainly glutamate and glutamine), ketone bodies, lactate and pyruvate. During fasting for instance, ketone bodies serve as an important fuel source gradually replacing glucose during the transition from fasting to starvation. Lactate is a particularly important mitochondrial substrate. It is dehydrogenated to pyruvate, which can then be fully oxidized by mitochondria to form $CO_2$. Oxidative metabolism of pyruvate is coupled to mitochondrial electron transport and respiration resulting in ATP synthesis. In the central nervous system, lactate also has a signaling function, stimulating for example hypoxia-induced factor 1a and down-stream signaling causing transcriptional changes in brain cells.

The source of lactate can be several fold. When neurons are electrically active, they accelerate their glycolytic pathway to the extent that mitochondria are no longer able to keep up with pyruvate oxidation. Instead, pyruvate is transiently converted to lactate in a process which has been termed aerobic glycolysis. In this situation, the accumulating lactate may exert its signaling role in neurons stabilizing for example hypoxia-induced factor 1α or inducing the expression of brain-derived neurotrophic factor, which is important for neuronal survival and long-term memory. A second and even more important source of lactate are astrocytes. This cell type is metabolically closely linked both to neurons and cerebral blood vessel capillaries. A main function of astrocytes is to sense synaptic activity and regulate the uptake as well as transfer of nutrients from the blood stream to neurons. Astrocytes are highly glycolytic. Their metabolism of glucose therefore mainly ends in the formation of lactate with only a fraction of pyruvate entering mitochondria for oxidation. Lactate synthesized by astrocytes is exported and taken up by neighboring neurons via monocarboxylate transporters. Here lactate serves as a fuel for neuronal mitochondria. This metabolic connection has been termed the astrocyte neuron lactate shuttle (ANLS).

A third source of lactate for the brain is the direct uptake from the periphery. During exercise systemic blood concentrations of lactate increase and cross the blood brain barrier to be metabolized by neurons. In this way, peripherally generated lactate contributes to brain energy metabolism. Exercise has been shown to improve memory function. Lactate may be an important metabolite explaining this effect of exercise on learning.

The importance of lactate on learning has been convincingly demonstrated when studying the ANLS. Lowering the expression of specific monocarboxylate transporters impairs the transfer of lactate from astrocytes to neurons and thereby long-term memory formation.

Modulation of lactate levels in the brain therefore has the potential to improve cognitive function. At the same time lactate either as a signaling molecule or as a fuel for mitochondria may influence neurological diseases where chronic or acute energy deficits need to be corrected. Alzheimer's disease (AD) is the most common cause of dementia. Currently, there is no cure for AD. Only symptomatic treatments exist, and these exert their beneficial effects mainly by restoring lowered neurotransmitter levels. Hypometabolism of glucose is a metabolic alteration likely occurring early during AD progression. Correction of brain metabolism is a promising approach to delay disease progression. Restoration of brain energy homeostasis was also found to restore mild cognitive impairment in the elderly.

Epilepsy is the fourth most common neurological disorder. Up to 30% of children with epilepsy continue to have seizures despite anticonvulsant treatment. Ketogenic diets successfully lower the frequency of seizures in children with intractable epilepsy. However, these diets are very high in fat and therefore highly unpalatable.

In epilepsy, local excessive electrical activity may result in the inability of neurons to cope with their energy load and the rapid provision of mitochondrial fuel may be beneficial. Transient formation of peripheral lactate or enhanced provision through the ANLS could be protective for neurons during recovery from a seizure.

Stroke is the most common cause of handicap and the third most common cause of death in adults worldwide. Tissue plasminogen activator (tPA) is the only Federal Drug Administration-approved treatment for ischemic stroke. The drawback of this treatment is that it can be effective only when administered during a short time window (within 3 hours) after ischemia. Endovascular procedure can be used to remove the clot blocking the artery but only after tPA treatment and within 6 hours of the ischemia. Strict criteria determine the eligibility of a patient for this procedure. Considering that only very limited treatment options exist, there is a need for new stroke treatments.

Targeting brain metabolism may prove useful in stroke for rapid restoration of energy supply as neurons are transiently deprived of oxygen and nutrients. In a preclinical model of stroke (transient middle cerebral artery occlusion), lactate has been successfully tested for its ability to prevent neuronal loss.

Taken together, modulating metabolism to enhance the availability of lactate for neurons may have beneficial effects in mild cognitive impairment during aging or neurological diseases with suspected energy deficits in neurons.

The inventors of the present application have identified unsaturated polyketides and macrocyclic lactones as bioactives that promote lactate secretion from astrocytes. These active compounds affect the astrocyte neuron lactate shuttle or stimulate lactate release from other tissues and may thereby be beneficial for brain energy homeostasis and neuronal health by counteracting the negative effects of impaired metabolism.

DETAILED DESCRIPTION

Definitions

As used in this disclosure and the appended claims, the singular forms "a," "an" and "the" include plural referents unless the context clearly dictates otherwise. Thus, for example, reference to "a component" or "the component" includes two or more components.

The term "analogue" as used herein are understood to refer to a compound having a structure similar to that of another one, but differing from it in respect of a certain component. A "derivative" is a compound that can be imagined to arise or actually be synthesized from a parent compound by replacement of one or more atoms with another atom or group of atoms.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

The components of the chemical structures described herein can be defined as follows: as used herein, the term "Unsaturated" means it contains at least one, maximum eight double bond between carbon atoms. "Modified polyketide" chain means that the original polyketide backbone has been further modified, biosynthetically and/or chemically. Such modifications may for example but not exclusively include reduction of carbonyl to hydroxyl groups, dehydration, double bond reduction, methyl oxidation to carboxylic acid, and cyclization to a macrocyclic lactone. "Dehydration" means a loss of water between two neighboring carbons, one bearing a hydroxyl and the other bearing at least one hydrogen, leading to the formation of a double bond. "Reduction" means addition of hydrogen to a double bond, leading to the formation of a single bond, typically reduction of a carbonyl to an alcohol, or an unsaturated chain to a saturated one. Carbon oxidation may be stepwise from a methyl to a alcohol, to an aldehyde, and finally to a carboxylic acid. "Cyclized chain" is related to a chain having atoms arranged in a ring or closed-chain structure. "Open chain" is a chain with a linear structure, i.e. having no ring in its structure.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 85 wt. % of the referenced components, most preferably at least 95 wt. % of the referenced components.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive.

The terms "food," "food product" and "food composition" or "diet product" mean a product or composition that is intended for ingestion by an individual such as a human and provides at least one nutrient to the individual. The compositions of the present disclosure, including the many embodiments described herein, can comprise, consist of, or consist essentially of the elements disclosed herein, as well as any additional or optional ingredients, components, or elements described herein or otherwise useful in a diet.

Cognitive function is responsible for brain functions including the processing of information, memory capacities, situation dependent judgment, learning ability and memory.

The terms "impaired memory function during aging" and "cognitive impairment during aging" as used herein means a reduction of cognitive function or impairment of any subcategory linked to brain function compared to the control healthy individual when using cognitive testing. Such cognitive testing usually includes measures of memory, language, ability to orient and attention span.

The term "polyketide" refers to a class of natural products produced by bacteria, fungi, and plants. Polyketides result from the stepwise addition of an extender molecule to a starter molecule until a chain of appropriate length is obtained. The extender is typically a malonate, a methylmalonate, or an ethylmalonate. The starter is classically acetate but a number of other organic acids can serve as a starter. For example, these can include linear and branched aliphatic acids like propionate, succinate, isobutyrate or aromatic acids like benzoate and cinnamate. The original polyketide chain can be further modified by reduction, dehydration, oxidation, and internal esterification (lactonisation).

The term "neurological disorder" as used herein means any disorder of the nervous system, particularly of the central nervous system. Such disorders can be the result of disease and accelerated loss of brain function during aging but could also be due to genetic variations or caused by malnutrition.

"Prevention" includes reduction of risk and/or severity of a condition or disorder. The terms "treatment," "treat," "attenuate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder, and include treatment of patients at risk of contracting a disease or suspected to have contracted a disease, as well as patients who are ill or have been diagnosed as suffering from a disease or medical condition. The term does not necessarily imply that an individual is treated until total recovery. These terms also refer to the maintenance and/or promotion of health in an individual not suffering from a disease but who may be susceptible to the development of an unhealthy condition. These terms are also intended to include the potentiation or otherwise enhancement of one or more primary prophylactic or therapeutic measure.

The terms "treatment," "treat," "attenuate" and "alleviate" are further intended to include the dietary management of a disease or condition or the dietary management for prophylaxis or prevention a disease or condition, by a diet product for example. A treatment can be patient- or doctor-related.

The term "individual" means any animal, including humans, that could suffer from a neurological disorder and thus benefit from one or more of the methods, compounds or compositions disclosed herein. Generally, the individual is a human or an avian, bovine, canine, equine, feline, hicrine, lupine, marine, ovine or porcine animal. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the individual is a human or a companion animal such as a dog or cat. A method, compound, or composition of the invention can be used for the prevention or treatment of disorders relating to brain health, particularly neurological disorders.

A human individual who is an older adult may benefit from one or more of the methods, compounds or compositions disclosed herein. The term "older adult" in the context of a human means an age from birth of at least 45 years, preferably above 50 years, more preferably above 55 years.

A human individual who is elderly may also benefit from one or more of the methods, compounds or compositions disclosed herein. The term "elderly" in the context of a human means an age from birth of at least 60 years, more preferably above 64 years, and most preferably above 68 years.

A human individual who is an infant may also benefit. The term "infant" in the context of a human means an age from birth of under 5 years.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "improved," "increased," "enhanced" and the like refer to the effects of the composition disclosed herein relative to a composition lacking one or more ingredients and/or having a different amount of one or more ingredients, but otherwise identical.

The terms "nutraceutical" combines the words "nutrition" and "pharmaceutical". It is a food or food product that provides health and medical benefits, including the prevention and treatment of disease. A nutraceutical is a product isolated or purified from foods that is generally sold in medicinal forms not usually associated with food. A nutraceutical is demonstrated to have a physiological benefit or provide protection against chronic disease. Such products may range from isolated nutrients, dietary supplements and specific diets to genetically engineered foods, herbal products, and processed foods such as cereals, soups, and beverages.

The term "nutraceutical" as used herein denotes usefulness in both nutritional and pharmaceutical fields of application. Thus, novel nutraceutical compositions can be used as supplements to food and beverages and as pharmaceutical formulations for enteral or parenteral application which may be solid formulations, such as capsules or tablets, or liquid formulations, such as solutions or suspensions.

COMPOUNDS OF THE INVENTION

The compounds of the invention have been demonstrated to promote lactate secretion.

The present invention relates to a compound of general structural formula (Ia)

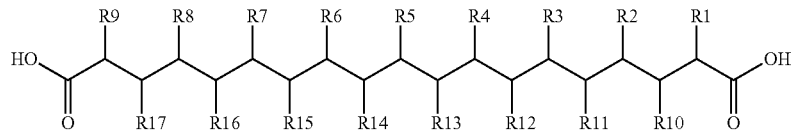

wherein R1 to R9 are individually selected from H and CH3; and
R10 to R17 are individually selected from H, C=O, and OH;
or a salt thereof for use in the promotion of lactate secretion.

In one embodiment, the compound of general structural formula (Ia) is further modified by reduction of carbonyl to hydroxyl groups.

In one embodiment, the compound of general structural formula (Ia) is further modified by dehydration.

In one embodiment, the compound of general structural formula (Ia) is further modified by at least one double bond reduction.

In one embodiment, the compound of general structural formula (Ia) is further modified by double bond reduction according to the following sequence of events:

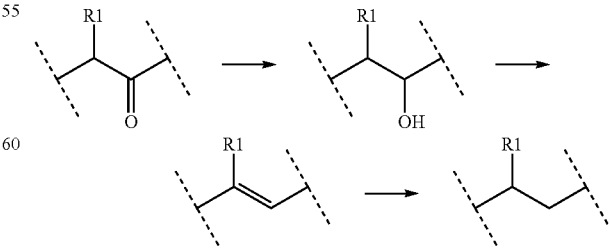

Methyl oxidation to carboxylic acid, and cyclization to a macrocyclic lactone are further potential modifications.

The structural variability of the chain may also arise from the incorporation of various starter units like isobutyrate, and/or various extender units like malonate or methylmalonate.

In one embodiment, the compound of structural formula (Ia) is modified to form the following structure:

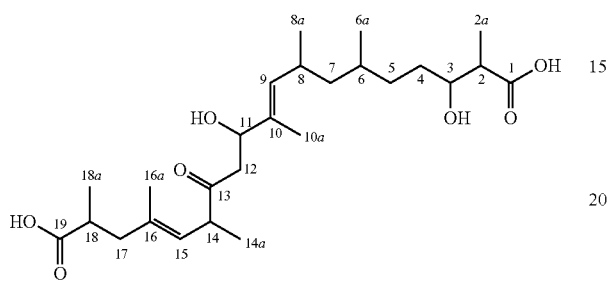

In one embodiment, the compound is a polyketide, particularly an unsaturated polyketide. In one embodiment, the compound has a molecular formula of C26H44O7. In one embodiment, the compound has a molecular weight of about 468 g/mol.

In another embodiment, the compound of structural formula (Ia) is lactonised between the carboxylic acid group at position 19 and the alcoholic group at position 3, creating an 18 atom ring to form compound A, as shown below:

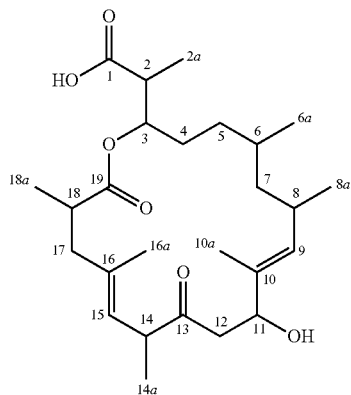

Compound A

In another embodiment, the compound of structural formula (Ia) is lactonised between the carboxylic acid group at position 19 and the alcoholic group at position 11, creating a 10 atom ring to form compound B, as shown below:

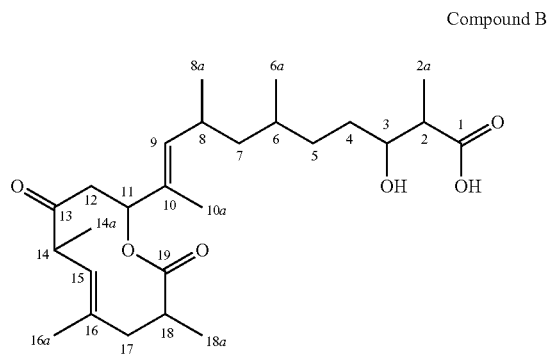 [SMILES: C/C1=C\C(C)C(=O)CC(/C(C)=C/C(C)CC(C)CCC(O)C(C)C(=O)O)OC(=O)C(C)C1]

Compound B

In another embodiment, the compound of structural formula (Ia) is lactonised between the carboxylic acid group at position 1 and the alcoholic group at position 11, creating a 12 atom ring to form compound C, as shown below:

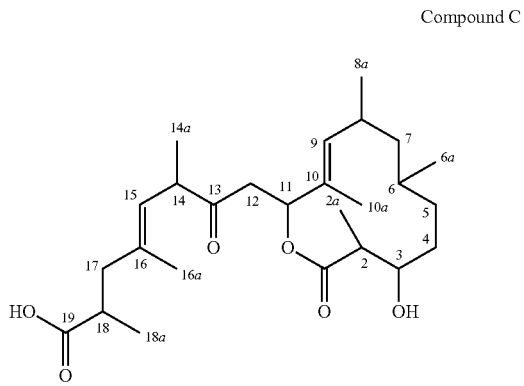 [SMILES: C/C(=C\C(C)C(=O)CC1OC(=O)C(C)C(O)CCC(C)CC(C)/C=C/1C)CC(C)C(=O)O]

Compound C

In one embodiment, the lactonised compound has a molecular formula of $C_{26}H_{42}O_6$. In one embodiment, the lactonised compound has a molecular weight of about 450 g/mol.

All compounds according to the invention can be used for the promotion of lactate secretion.

In one embodiment, the compound is for use in the prevention and/or treatment of a neurological disorder in an individual wherein lactate secretion is promoted.

In one embodiment, the compound is for use in the prevention and/or treatment of a neurological disorder in an individual wherein lactate secretion from astrocytes is promoted.

In one embodiment, the compound is for use in the prevention and/or treatment of a neurological disorder in an individual wherein lactate secretion from peripheral tissues is promoted.

In one embodiment, the compound is for use in the prevention of cognitive decline in an individual wherein lactate secretion is promoted, particularly from astrocytes.

In one embodiment, the individual is a human. In one embodiment, the individual is an older adult human. In one embodiment, the individual is an elderly human. In one embodiment, the individual is an infant human.

In one embodiment, the individual is a companion animal.

In one embodiment, the compound is an unsaturated polyketide or a macrocyclic lactone. In one embodiment, the compound can be found in nature. In one embodiment, the compound is generally regarded as safe (GRAS) and non-toxic to a human or companion animal.

There is also provided a composition, particularly an improved composition, comprising an effective amount of the compound of the invention, for use in the promotion of lactate secretion.

There is also provided a composition, particularly an improved composition, comprising an effective amount of the compound of the invention, for use in the promotion of lactate secretion in an individual.

There is also provided a composition, particularly an improved composition, comprising an effective amount of the compound of the invention, for use in the promotion of lactate secretion thereby preventing or treating a neurological disorder in an individual.

In one embodiment, said composition is a pharmaceutical or nutraceutical composition.

There is also provided a food or food extract enriched with a compound or composition of the invention.

Use of the Compound for the Prevention or Treatment of Neurological and Other Disorders The compound of the invention can be used for the prevention or treatment of a neurological disorder, for memory dysfunction or for mild cognitive impairment in an individual. In one embodiment, the compound of the invention can be used for the prevention or treatment of memory dysfunction in an individual. In one embodiment, the compound of the invention can be used for the prevention or treatment of mild cognitive impairment in an individual.

Examples of a neurological disorder include disorders of the central nervous system such as addiction; arachnid cysts; attention deficit/hyperactivity disorder (ADHD); Autism; Bipolar disorder; Catalepsy; Depression; Encephalitis; Epilepsy/Seizures; Infection; Locked-in syndrome; Meningitis; Migraine; Multiple sclerosis; Myelopathy. Neurological disorders may also include neurodegenerative disorders such as Alzheimer's disease, Huntington's disease, Parkinson's disease, and Tourette's syndrome. The compound of the invention may be used for the prevention or treatment of one or more of these neurological disorders.

In some embodiments, the compound of the invention can also be used for the prevention or treatment of diabetes and/or diabetes-related disorders, particularly Type 11 diabetes, counteracting of insulin resistance, complications of diabetes, protection of pancreatic Langerhans islet beta-cells, antidiabetic therapies, therapy of syndrome X, diabetic neurosis, diabetic nephropathy, diabetic retinopathy, and for lifestyle-related diseases in an individual.

In some embodiments, the compound of the invention can also be used for the prevention or treatment of disorders relating to lipid metabolism, particularly to those of the ligand of retinoid X receptor, ligand of nuclear receptor, PPAR-Agonist, PPAR-Antagonist, ligands activating nuclear receptor super family, and to the improvement of lipid metabolism, and antilipemic disease in an individual.

In some embodiments, the compound of the invention can also be used for the prevention or treatment of disorders related to vascular complications, particularly arteriosclerosis, hypertension, cerebrovascular diseases, hypotensive, hypertension, and cerebrovascular disorders in an individual.

In some embodiments, the compound of the invention can also be used for the prevention or treatment of cancer, particularly to control tumors, and digestive cancers in an individual.

In some embodiments, the compound of the invention can also be used for the prevention or treatment of inflammatory diseases, particularly rheumatoid arthritis, chronic inflammation, vascular chronic inflammation and the like in an individual.

In some embodiments, the compound of the invention can also be used as a stimulator of AMPK activity in an individual.

In some embodiments, the compound of the invention can also be used for the prevention or treatment of a series of other disorders, including autoimmune diseases, anorectic, restenosis, myxedema, and cachexia in an individual.

The present invention also relates to the use of a compound of the invention in the preparation of a product for the prevention or treatment of a neurological disorder in an individual.

The present invention also relates to the use of a compound of the invention in the preparation of a diet product.

The present invention also relates to a method for the prevention or treatment of a neurological disorder comprising administering a compound of the invention to an individual.

EXAMPLES

The invention can be illustrated by way of the following examples, which should not be seen as limiting the scope of the invention.

Example 1

Lactate Release—Screening Assay

FIG. 1 shows the lactate screening strategy and the general workflow of the lactate release from the astrocytes drug discovery screen.

Human astrocytoma cell line CCF-STTG1 was cultured at 37° C. in a humidified atmosphere (5% CO2) in RPMI-1640 medium supplemented with 10% (v/v) heat-inactivated fetal calf serum, 50 µg/ml penicillin and 100 µg/ml streptomycin.

CCF-STTG1 were seeded in 384-well plates. Two days later, the cells were washed 3 times and incubated 30 min in Krebs-Ringer bicarbonate HEPES (KRBH) buffer containing (in mM): 140 NaCl, 3.6 KCl, 0.5 NaH2PO4, 0.5 MgSO4, 1.5 CaCl2, 10 HEPES, 5 NaHCO3 (pH7.4) supplemented with 2.5 mM glucose. Then, the cells were maintained in the buffer in the presence of tested compounds. Supernatants were collected after 2 hours and were assessed for lactate concentration. Lactate concentration in the supernatants were determined by fluorescent enzymatic assay. Samples were diluted in assay reagent containing (in mM or U/ml)): 100 sodium phosphate (pH7.5), 0.1 EDTA, 0.05 Amplex UltraRed, 0.1 Lactate oxidase, 1.5 Horseradish Peroxidase.

Fluorescence emission was measured at 600 nm after an excitation at 500 nm using Bioteck Synergie Neo multimode reader after 30 min at room temperature protected from direct light.

Example 2

Lactate Release—Counter Screen Assay

The compounds were also tested in absence of cells using the same fluorescent enzymatic assay described previously to assess their auto fluorescence or their interaction with the enzymatic assay. Fluorescence emission was measured at 600 nm after an excitation at 500 nm using Bioteck Synergie Neo multimode reader after 30 min at room temperature and protected from direct light. Fluorescence was then compared to control fluorescence obtained in basal and stimulated cells.

For the drug discovery counter screen, compounds diluted in KRBH were assessed for lactate release. The identified unsaturated polyketide or macrocyclic lactone compounds had no effect on the enzymatic assay in the absence of cells.

Example 3

Lactate Release—Orthogonal Assay

CCF-STTG1 were seeded in 384-well plates. Two days later, the cells were washed 3 times and incubated 30 min in Krebs-Ringer bicarbonate HEPES (KRBH) buffer containing (in mM): 140 NaCl, 3.6KCl, 0.5 NaH2PO4, 0.5 MgSO4, 1.5 CaCl2), 10 HEPES, 5 NaHCO3 (pH7.4) supplemented with 2.5 mM glucose. The cells were maintained in the buffer in the presence of tested compounds. Supernatants were collected after 2 hours and assessed for lactate concentration. Lactate concentration in the supernatant was determined by a spectrophotometric enzymatic assay (lactate colorimetric assay kit II no. K627; BioVision, Milpitas, Calif. USA). In this kit, lactate is oxidized by lactate dehydrogenase to generate a product which interacts with a probe to produce a color ($\lambda$max=450 nm).

Absorbance was measure after 30 min at 450 nm using Bioteck Synergie Neo multimode reader. Background absorbance obtained in the absence of kit was subtracted from each value.

The stimulation of lactate secretion after treatment with unsaturated polyketide/macrocyclic lactone compounds was confirmed in an orthogonal assay based on another enzyme to measure lactate. The results of the lactate release measurement during the drug discovery screen for each compound and the results of lactate release measure with the orthogonal assay were correlated.

Dose response curves were established for compounds identified in the screen to stimulate lactate secretion. The EC50 values for the stimulation of lactate secretion were determined using primary human IPS cell derived astrocytes.

Differentiated human iPSCs (iCell astrocytes, and iCell cardiomyocytes) were obtained from Cellular Dynamics International (CDI, Madison, Wis., USA). iCell astrocytes were cultured in DMEM supplemented with 10% fetal calf serum and N2 complement. iCell cardiomyocytes were maintained in a medium supplied by CDI. Cell cultures were kept in a humidified atmosphere (5% CO2) at 37° C.

FIG. 2 shows lactate release. Dose response of compounds on lactate release from human iPSc derived into astrocyte fitted with a log (agonist) vs response variable slope to extract efficacy (EC50). Mean±SEM in duplicate.

Example 4

Toxicity—ATP Content iCell Cardiomyocytes were seeded in 384-well plates. Eight days later cells were treated for 24 hours with compounds. Cell viability was determined by the quantification of intracellular ATP after cell lysis. ATP was used as an indicator of metabolically active cells. ATP was measured using a luminescent cell viability assay (CellTiter-Glo®; BioRad, Hercules, Calif., USA). Luminescence was measured after 20 min in a Bioteck Synergie Neo multimode reader.

Toxicity of the unsaturated polyketide/macrocyclic lactone compounds were evaluated in human IPS cell derived cardiomyocytes by measuring total ATP in cell lysates. Dose response experiments revealed that unsaturated polyketide/macrocyclic lactone compounds stimulated lactate secretion from astrocytes at concentrations several orders of magnitude below the concentration where they caused toxicity in cardiomyocytes.

FIG. 3 shows toxicity. Dose response of compounds on human iPSc derived into cardiomyocyte with evaluation of the ATP level using cell titer glow. Results were normalized between untreated cells (100%) and positive control (0%).

Example 5

Identification—MS and NMR

Acquisition of MS and MS/MS data of the unsaturated polyketide/macrocyclic lactone were performed in positive and negative ionization modes using a Q-Exactive mass spectrometer (Thermo Scientific, Bremen, Germany) with a heated electrospray ionization (HESI) source. Ionization source parameters were the following: capillary voltage 4.3 kV and 4.0 kV in positive and negative modes respectively; capillary and probe heater temperature: 350° C.; sheath gas ($N_2$): 45.0 unit; auxiliary gas: 15.0 unit; spare gas: 1.0; S-Lens RF level: 50.0. A data dependent analysis was performed using a list of inclusion containing m/z 451.30 (positive ionization mode) and 449.29 (negative ionization mode), otherwise, data dependent MS/MS events were performed on the 5 most intense ions detected in full scan MS with a dynamic exclusion time of 1.0 s. Settings of full MS experiments were as follows: MS resolution: 70000; maximum number of injection time: 100 ms; scan range 100 to 1000 m/z, while data-dependent analysis settings were set as follow: MS resolution: 17500; maximum number of injection time: 50 ms; isolation window: 4.0 m/z; stepped normalized collision energy (NCE): 10, 20, 30 units. Data were acquired in centroid mode.

FIGS. 4 A, B, C and D show MS and MS/MS data in positive and negative ionization modes.

Table 1 and Table 2 show the 20 most intense MS/MS signals relative to the fragmentation of the unsaturated polyketide/macrocyclic lactone in positive and negative ionization modes respectively.

TABLE 1

| m/z | Relative intensity |
|---|---|
| 95.08574 | 15.36 |
| 109.10108 | 15.75 |
| 113.05945 | 13.51 |
| 121.10087 | 14.48 |
| 137.09550 | 18.06 |
| 153.12674 | 44.26 |
| 155.10591 | 42.08 |
| 161.13200 | 14.03 |
| 177.16301 | 17.62 |
| 181.12155 | 100.00 |
| 189.16321 | 18.06 |
| 199.13200 | 66.25 |
| 217.15781 | 13.02 |
| 235.16830 | 19.88 |
| 277.17859 | 23.85 |
| 369.27722 | 13.28 |
| 387.28735 | 35.76 |
| 397.27225 | 16.56 |
| 415.28220 | 28.01 |
| 433.29239 | 25.00 |

TABLE 2

| m/z | relative intensity |
|---|---|
| 71.05014 | 43.54 |
| 72.05344 | 1.74 |
| 73.02963 | 0.19 |
| 92.26414 | 0.46 |
| 153.12820 | 2.10 |
| 197.11790 | 100.00 |
| 198.12122 | 13.80 |
| 199.12320 | 1.11 |

TABLE 2-continued

| m/z | relative intensity |
|---|---|
| 261.22186 | 4.09 |
| 262.22510 | 0.60 |
| 343.30042 | 1.08 |
| 344.30417 | 0.17 |
| 387.28976 | 13.71 |
| 388.29282 | 3.83 |
| 389.29739 | 0.60 |
| 405.29950 | 4.01 |
| 406.30267 | 1.35 |
| 407.30615 | 0.18 |
| 431.27869 | 0.18 |
| 444.85123 | 0.16 |

The NMR experiments were recorded on a Bruker Avance III HD 600 MHz NMR spectrometer equipped with a QCI 5 mm Cryoprobe and a SampleJet automated sample changer (Broker BioSpin, Rheinstetten, Germany). Spectra were recorded in $CDCl_3$ and DMSO-$_{d6}$. Chemical shifts are reported in parts per million (δ) using the residual signal solvent at 7.26 and 77.16 (or 2.50 and 39.52) for $^1H$ and $^{13}C$ NMR, respectively, and coupling constants (J) are reported in Hz. Complete assignment was performed based on 2D experiments (COSY, edited-HSQC, HMBC and ROESY).

FIGS. 5 A, B, C, D, E, F, G, H, I and J show 1D and 2D NMR spectra of the unsaturated polyketide/macrocyclic lactone in deuterated chloroform ($CDCl_3$) and/or in deuterated DMSO (DMSO-$_{d6}$)

Table 3 shows $^1H$ (600 MHz) and $^{13}C$ NMR (151 MHz) spectroscopic data of the unsaturated polyketide/macrocyclic lactone in CDCl3.

TABLE 3

| No | δ$_H$ (Multiplicity, J) | δ$_C$ | HSQC-EDITED | HMBC | COSY | NOESY |
|---|---|---|---|---|---|---|
| 1 | — | 174.7 | — | — | — | — |
| 2 | 2.77 (p, 7.1 Hz)) | 41.2 | 2 | 1, 2a, 3 | 2a, 3 | 3, 5" |
| 2a | 1.19 (d, 7.1 Hz) | 13.3 | 2a | 1, 2, 3 | 2 | 3 |
| 3 | 5.11 (dt, 8.3, 4.3 Hz) | 73.7 | 3 | 5 | 2 | 2, 2a, 4", 4' |
| 4' | 1.69 (m) | 28.9 | 4 | — | 4" | 3 |
| 4" | 1.44 (m) | 28.9 | 4 | — | 4' | 3, 15 |
| 5' | 1.56 (m) | 28.8 | 5 | — | 5" | — |
| 5" | 0.95 (m) | 28.8 | 5 | — | 5' | 2 |
| 6 | 1.28 (m) | 29.7 | 6 | — | 6a | — |
| 6a | 0.83 (d, 6.5 Hz) | 21.1 | 6a | 5, 6, 7 | 6 | — |
| 7' | 1.26 (m) | 46.3 | 7 | — | 8 | 9 |
| 7" | 1.20 (m) | 46.3 | 7 | — | 8 | 9 |
| 8 | 2.45 (m) | 29.1 | 8 | — | 7", 7', 8a, 9 | 10a |
| 8a | 0.93 (d, 6.8 Hz) | 21.9 | 8a | 7, 8 | 8 | 9 |
| 9 | 5.18 (d, 8.6) | 135.3 | 9 | 7, 10a, 11 | 8 | 7", 7', 8a, 11 |
| 10 | — | 134.3 | — | — | — | — |
| 10a | 1.61 (d, 1.3 Hz) | 9.9 | 10a | 9, 10, 11 | — | 8, 12", 12', 15 |
| 11 | 4.58 (dd, 8.4, 6.0 Hz) | 75 | 11 | 9, 10a, 12 | 12', 12" | 9, 12", 12' |
| 12' | 2.92 (dd, 15.6, 8.4 Hz) | 45.4 | 12 | 10, 11, 13 | 11, 12" | 10a, 11, 14 |
| 12" | 2.41 (dd, 15.6, 6.0 Hz) | 45.4 | 12 | 10, 11, 13 | 11, 12' | 10a, 11, 14 |
| 13 | — | 209.7 | — | — | — | — |
| 14 | 3.23 (dt, 10.3, 6.6 Hz) | 47.7 | 14 | 13, 14a, 15, 16 | 14a, 15 | 12", 12', 15, 16a |
| 14a | 0.98 (d, 6.6 Hz) | 14.5 | 14a | 13, 14, 15 | 14 | 15 |
| 15 | 4.74 (d, 10.3 Hz) | 124.9 | 15 | 13, 14, 16a, 17 | 14 | 4", 10a, 14, 14a, 17", 17', 18 |
| 16 | — | 136.6 | — | — | — | — |
| 16a | 1.77 (d, 1.5 Hz) | 16.9 | 16a | 15, 16, 17 | — | 14, 18 |
| 17' | 2.30 (dd, 13.5, 11.5 Hz) | 44.1 | 17 | 15, 16, 16a, 18, 18a, 19 | 17", 18 | 15, 18a |
| 17" | 2.14 (dd, 13.5, 3.0 Hz) | 44.1 | 17 | 15, 16, 18, 18a, 19 | 17' | 15, 18a |
| 18 | 2.68 (ddd, 11.5, 6.9, 3.0 Hz) | 40.5 | 18 | — | 17', 18a | 15, 16a |
| 18a | 1.23 (d, 6.9 Hz) | 18.3 | 18a | 17, 18, 19 | 18 | 17", 17' |

After analysis of all the COSY, HSQC and HMBC correlations (FIG. 5 C to E), a first linear structure was elucidated. The $^1H$ and $^{13}C$ chemical shifts as well as the 2D correlation are described in Table 3.

In order to fit with the molecular weight of 450 g/mol, a cyclisation was required. Two hydroxyl groups and two acids were available to form an ester. Because of its downfield chemical shift the hydroxymethine H-3 at δH 5.11 was preferred to that at δH 4.58 (H-11). The formation of an ester between C-1 and H-3 was unlikely, as it will give a four membered ring. A cyclisation between H-3 and the acid in C-19 was thus proposed, illustrated herein as compound A. A HMBC correlation between H-3 and C-19 was expected but even after the recording of a longer HMBC spectrum with 64 scans (FIG. 5 G) no crosspeak was observed.

In an attempt to observe hydroxyl group, the compound was dried and solubilized in 60 uL of DMSO-$d_6$. Then, the NMR spectra (FIG. 5 H to J) were measured in 1.7 mm tube. Unfortunately, no mobile proton was observed and no additional HMBC correlation compared to the spectra recorded in $CDCl_3$.

The NOESY correlations observed between CH3-10a and H-8, H-9 and H-11, CH3-16a and H-14, H-15 and H-17 (FIG. 5 F) indicated that the configuration of the double bonds were E. The configuration of the other stereocenters were not determined.

Example 6

Hit Evaluation

Table 4 and Table 5 show the compounds of interest

TABLE 4

| Fraction number | Primary screen % | Orthogonal assay % | Reconfirmation % |
|---|---|---|---|
| Fraction 8 | 73 | 57 | 94 |
| Fraction 9 | 103 | 69 | 115 |

TABLE 5

| | Astrocytes Lactate release | | Cardiomyocytes Toxicity | |
|---|---|---|---|---|
| Fraction or CAS Number | EC50 [mg/ml or M] | logEC50 | IC50 [mg/ml or M] | log IC50 |
| Fraction 8 | 3.7E−07 | −6.4 | 5.9E−03 | −4.2 |
| Fraction 7 | | No activity | | |
| Fraction 8 (second batch) | 1.0E−06 | −6.0 | Not tested | |
| Fraction 9 (second batch) | 9.5E−07 | −6.0 | Not tested | |
| Fraction 10 | 4.9E−06 | −5.3 | Not tested | |
| unsaturated polyketide/ macrocyclic lactone | 1.6E−06 | −5.7 | >1.0E−04 | >−4.0 |

The unsaturated polyketide/macrocyclic lactone compound mentioned throughout the Examples section is proposed to have the structure corresponding to Compound A as described herein. The toxicity expressed in log IC50 (ATP content after 24 hours compound treatment on human iPSc derived into cardiomyocyte) was compared against the lactate release in log EC50 (lactate secretion after 2 hours compound treatment in human iPSc derived into astrocytes).

Unsaturated polyketide/macrocyclic lactone tested compounds showed a range of concentrations where they are active on lactate secretion by astrocytes and not toxic on cardiomyocytes.

A. Fraction 8 containing unsaturated polyketide/macrocyclic lactone $C_{26}H_{42}O_6$; B. pure unsaturated polyketide/macrocyclic lactone.

Figure 1:
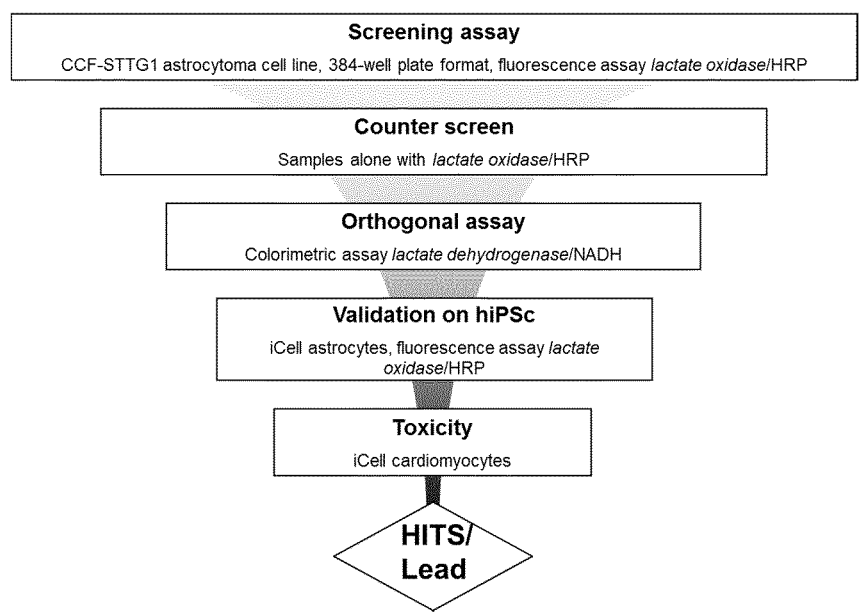
FIG. 1 shows the lactate screening strategy
Figure 2:
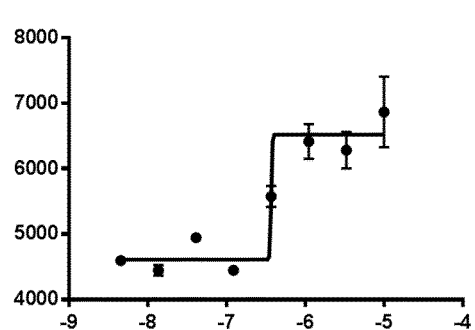
FIG. 2 shows lactate release. Y-axis: relative fluorescence unit, X-axis: logarithm concentration of the compound in mg/ml for fraction and molar for pure compound. A. Fraction 8 containing unsaturated polyketide/macrocyclic lactone; B. Fraction 8 containing unsaturated polyketide/macrocyclic lactone (Second batch); C. Fraction 9 containing unsaturated polyketide/macrocyclic lactone; D. Fraction 10 containing unsaturated polyketide/macrocyclic lactone $C_{26}H_{42}O_6$; E. Pure unsaturated polyketide/macrocyclic lactone No CAS number attributed (new chemical entity), proposed to have a structure corresponding to compound A as described herein.
Figure 2:
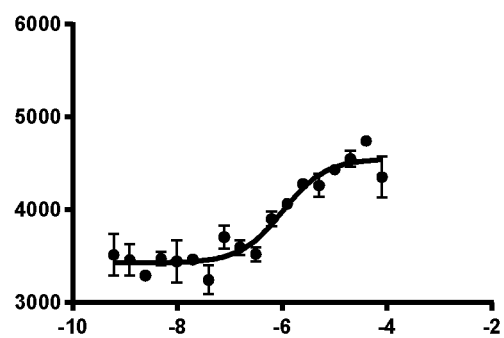
Figure 2:
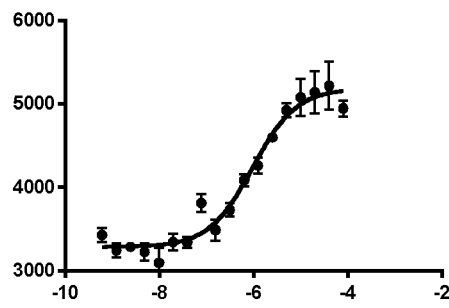
Figure 2:
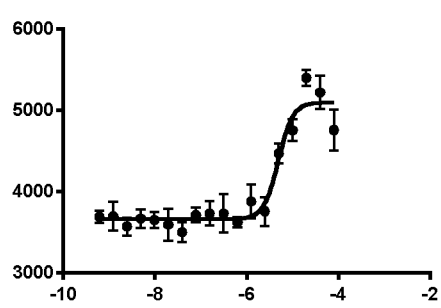
Figure 2:
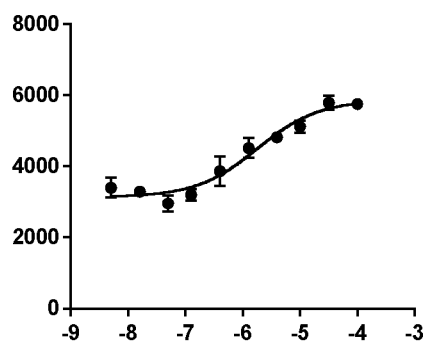
Figure 3:
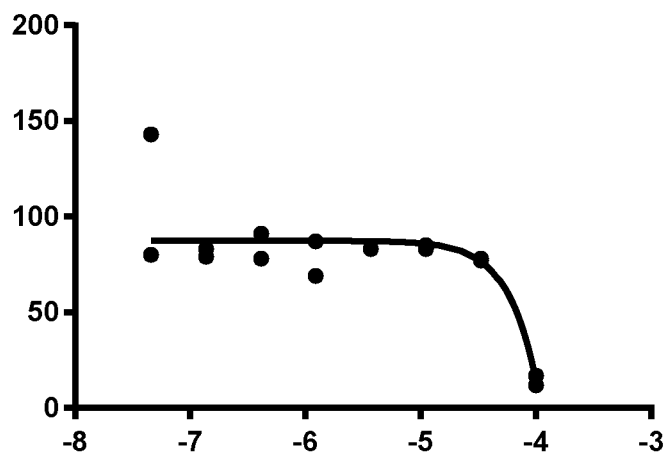
FIG. 3 shows toxicity. Y-axis: relative fluorescence unit in percentage, X-axis: logarithm concentration of the compound in mg/ml for fraction and molar for pure compound.
Figure 3:
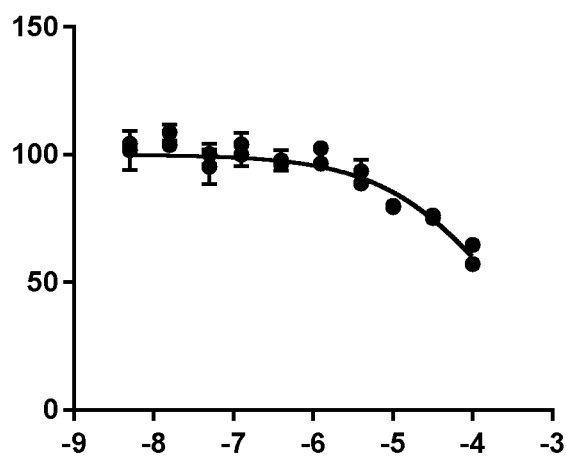
Figure 4:
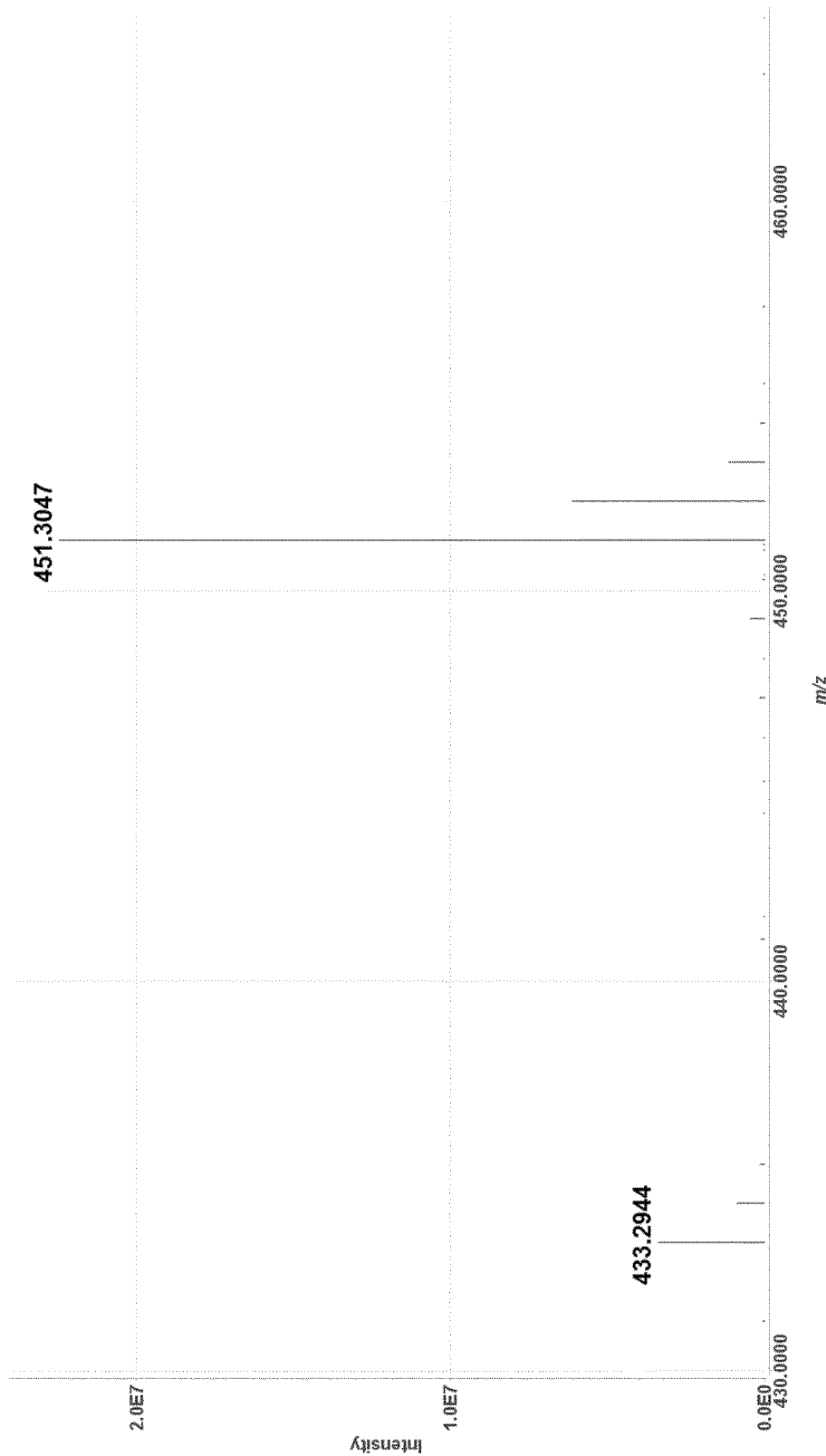
Figure 4B:
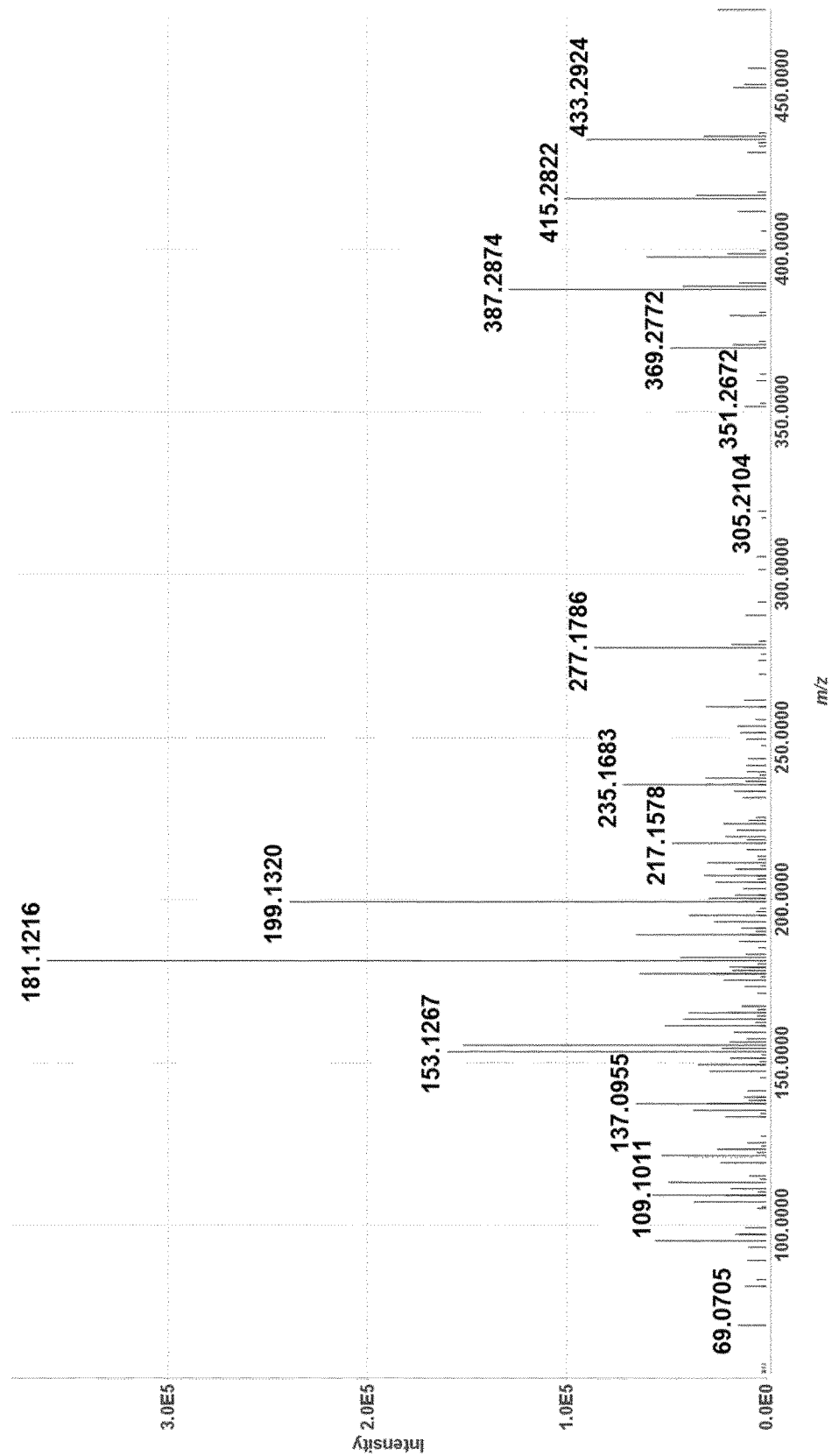
Figure 4C:
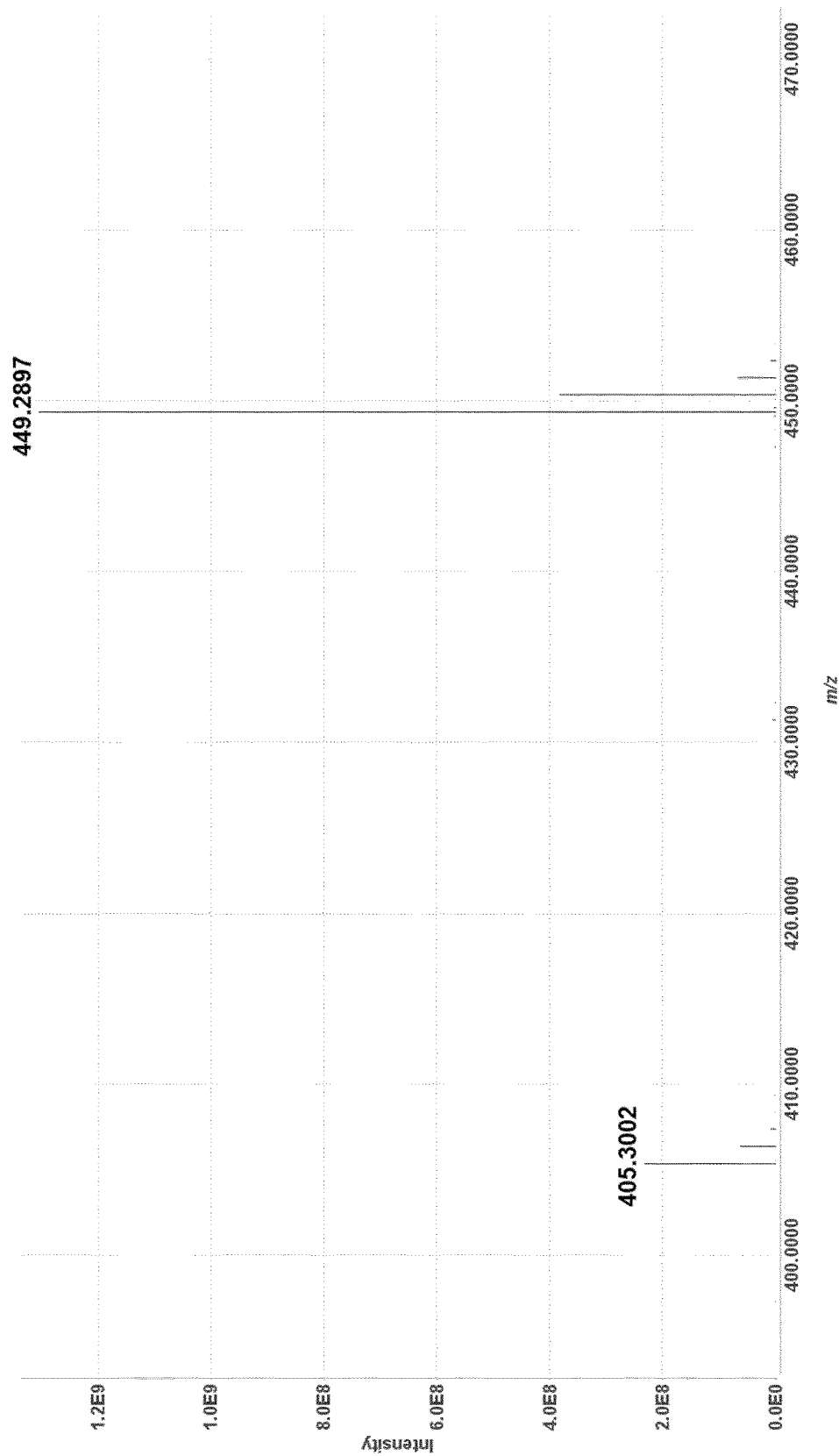
Figure 4D:
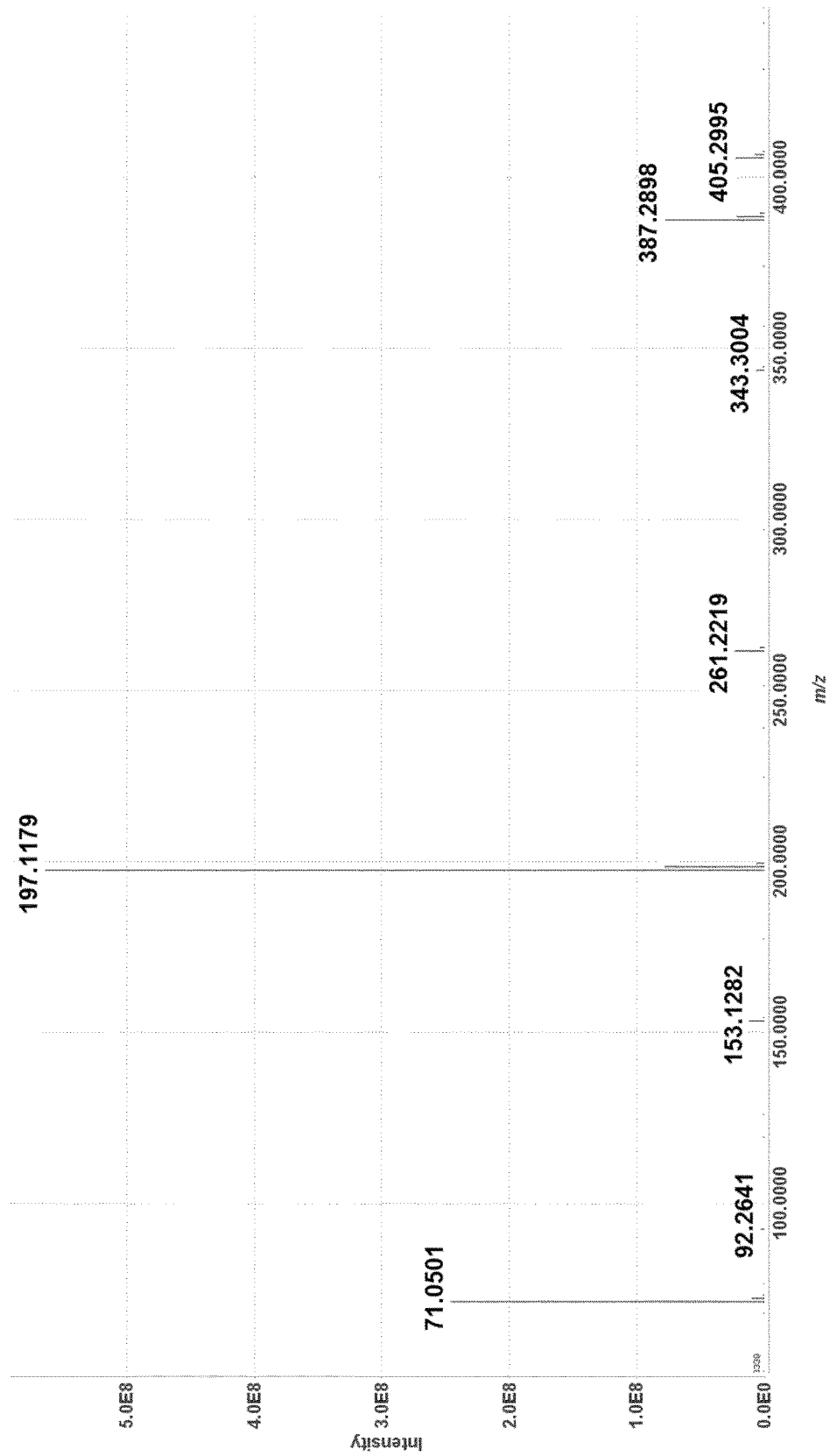

FIG. 4 shows MS and MS/MS data. Y-axis: ion intensity, X-axis: mass-to-charge ratio (m/z). A. MS spectra of the unsaturated polyketide/macrocyclic lactone in positive ionization mode (m/z 451.30); B. MS/MS spectra of the unsaturated polyketide/macrocyclic lactone in positive ionization mode; C. MS spectra of the unsaturated polyketide/macrocyclic lactone in negative ionization mode (m/z 449.29); D. MS/MS spectra of the unsaturated polyketide/macrocyclic lactone in negative ionization mode.

Figure 5:
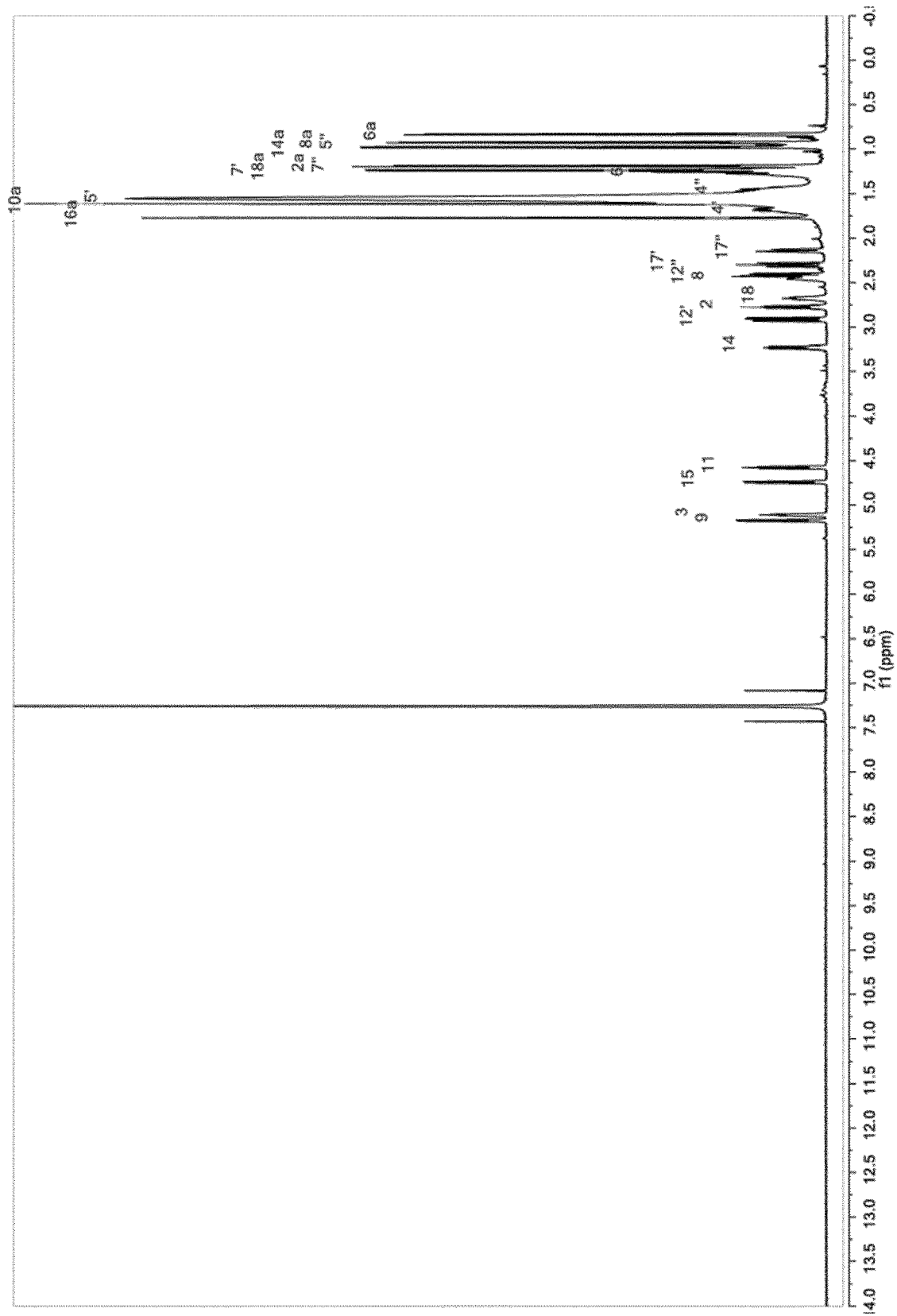
Figure 5B:
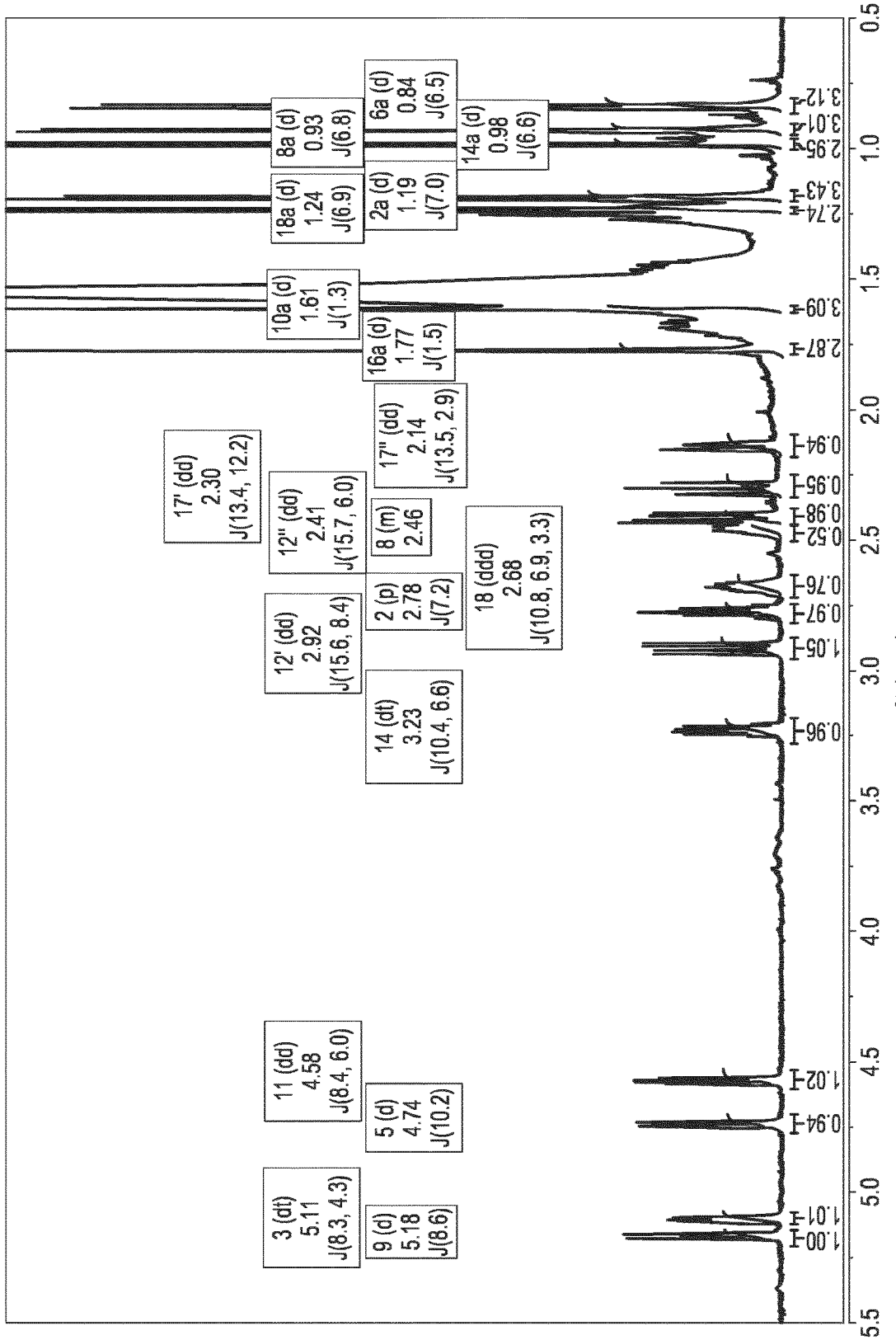
Figure 5C:
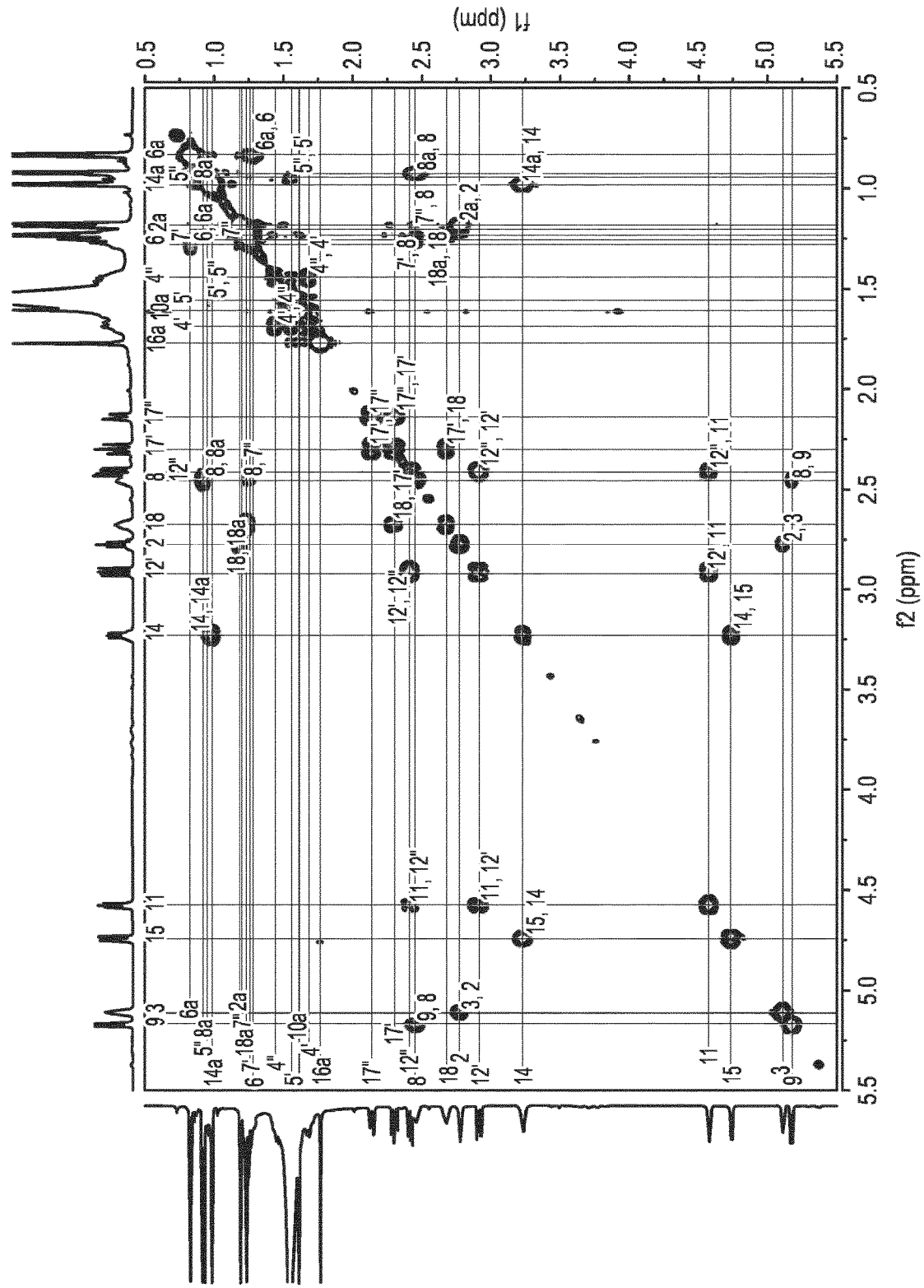
Figure 5D:
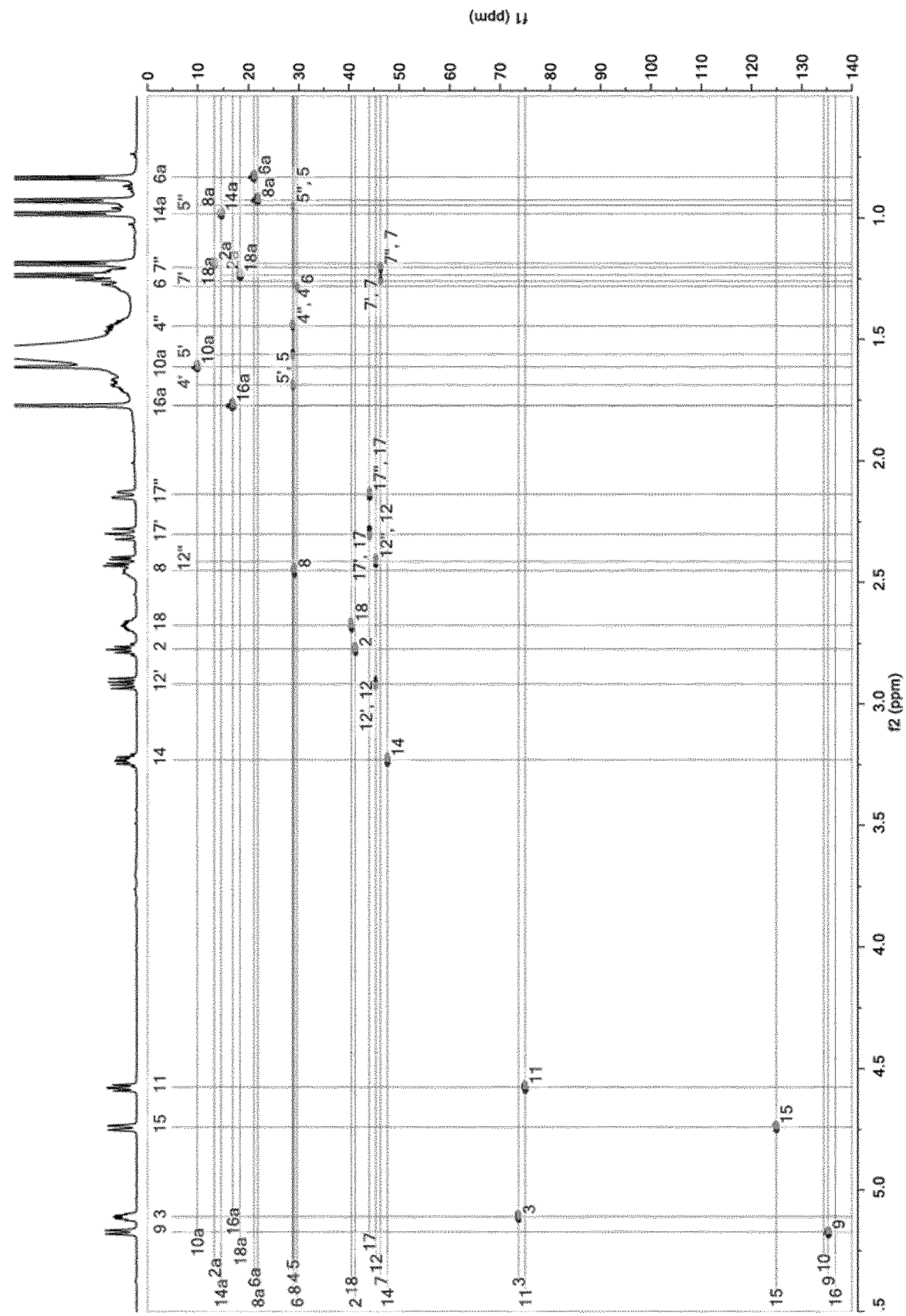
Figure 5E:
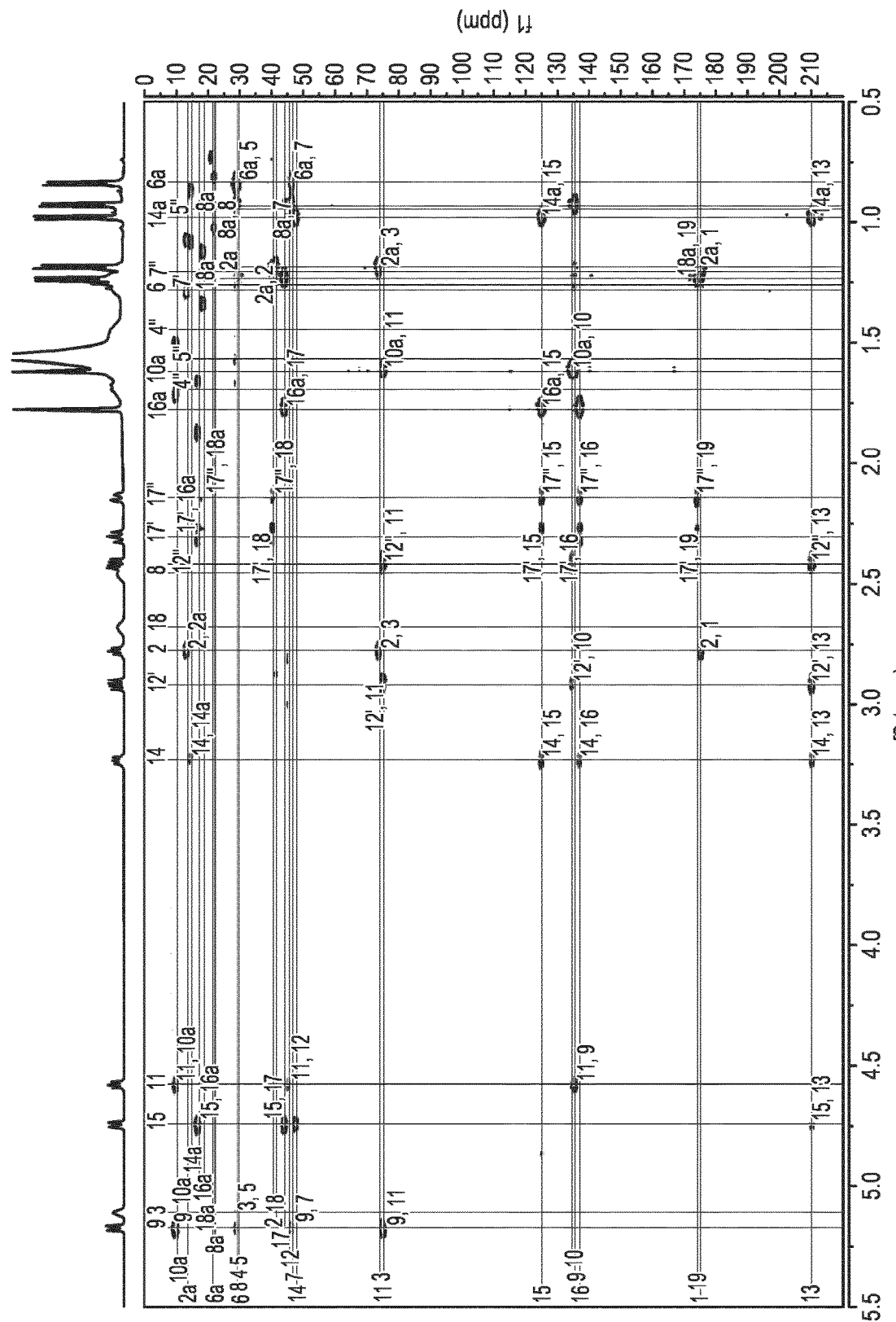
Figure 5F:
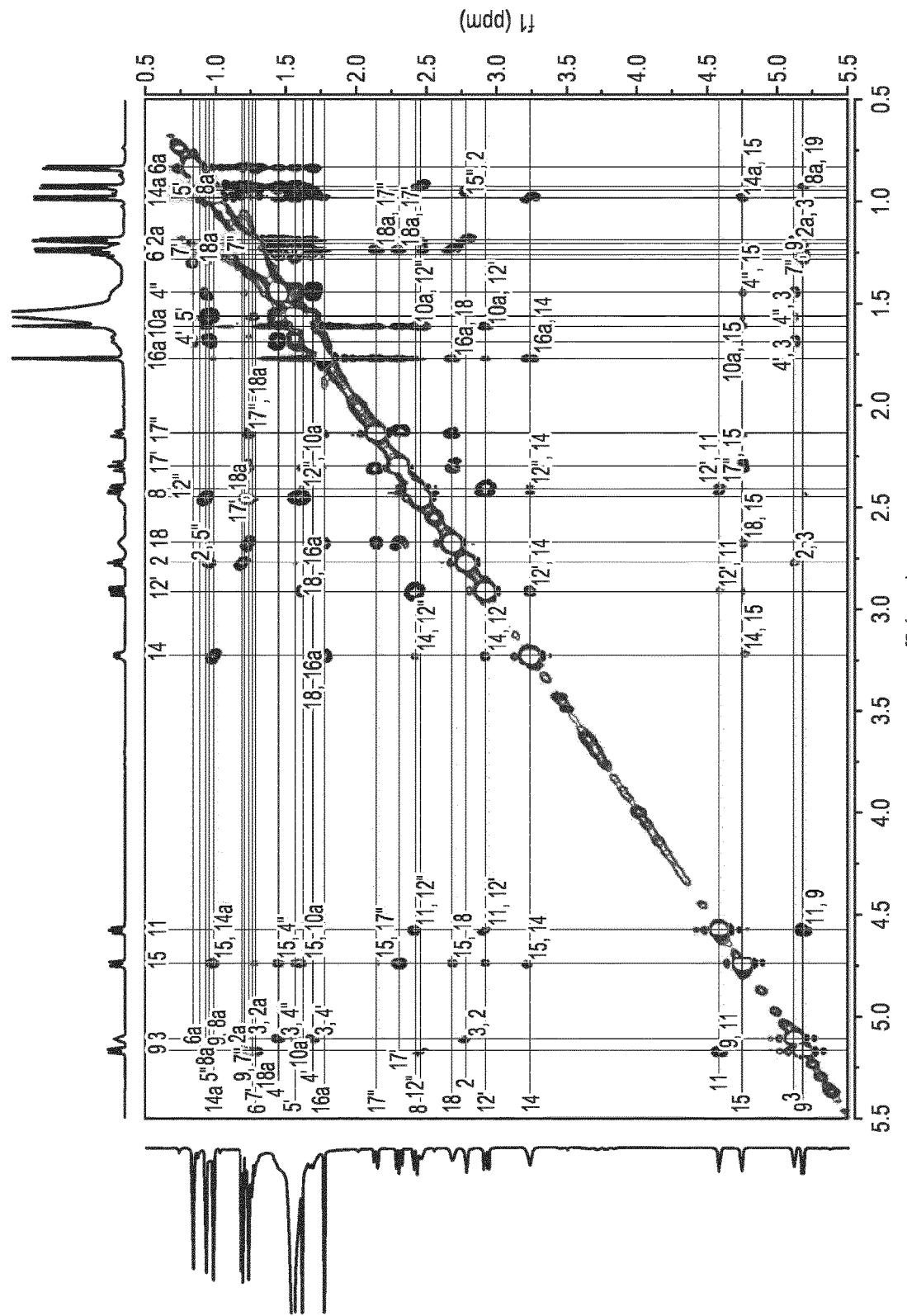
Figure 5G:
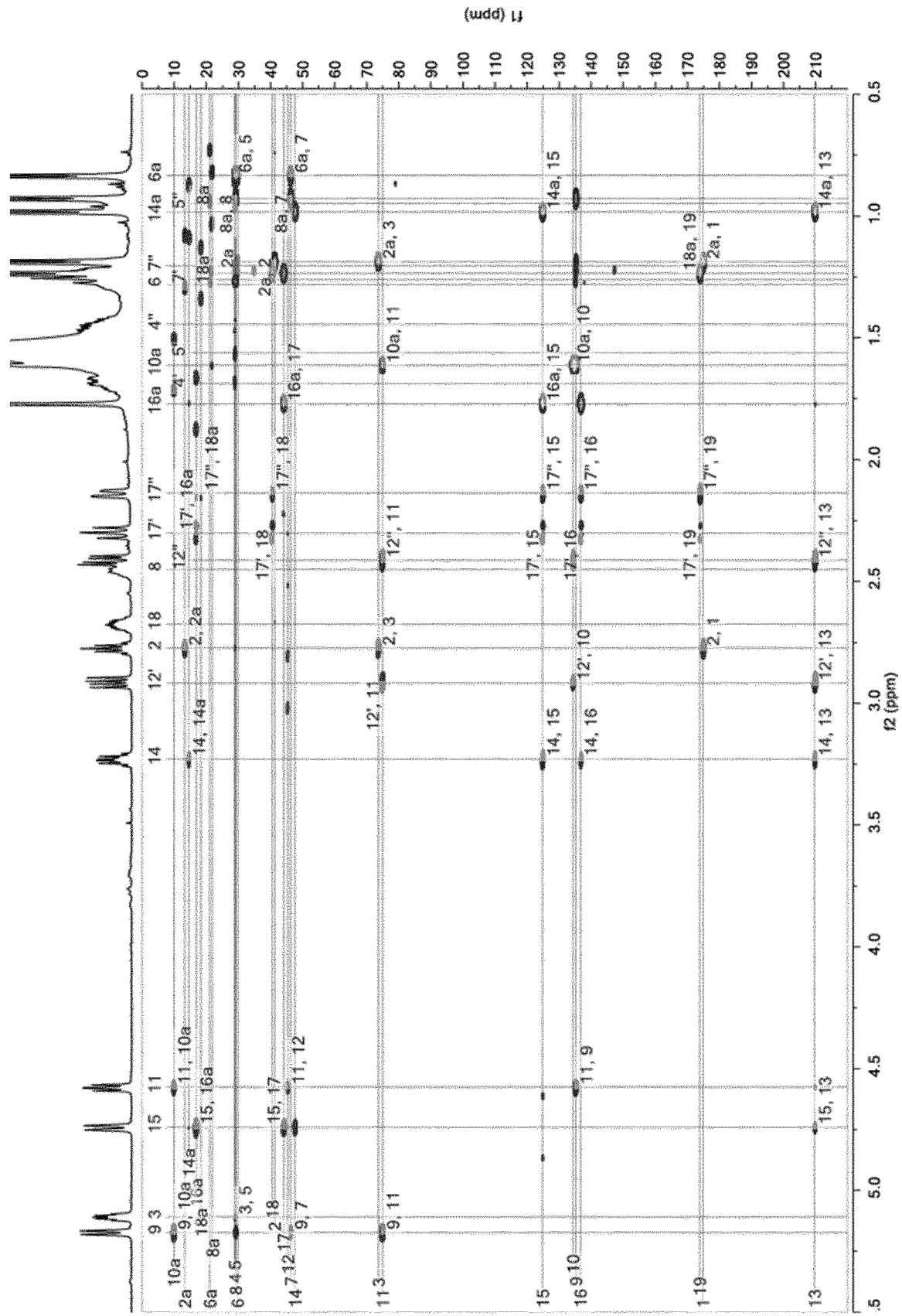
Figure 5H:
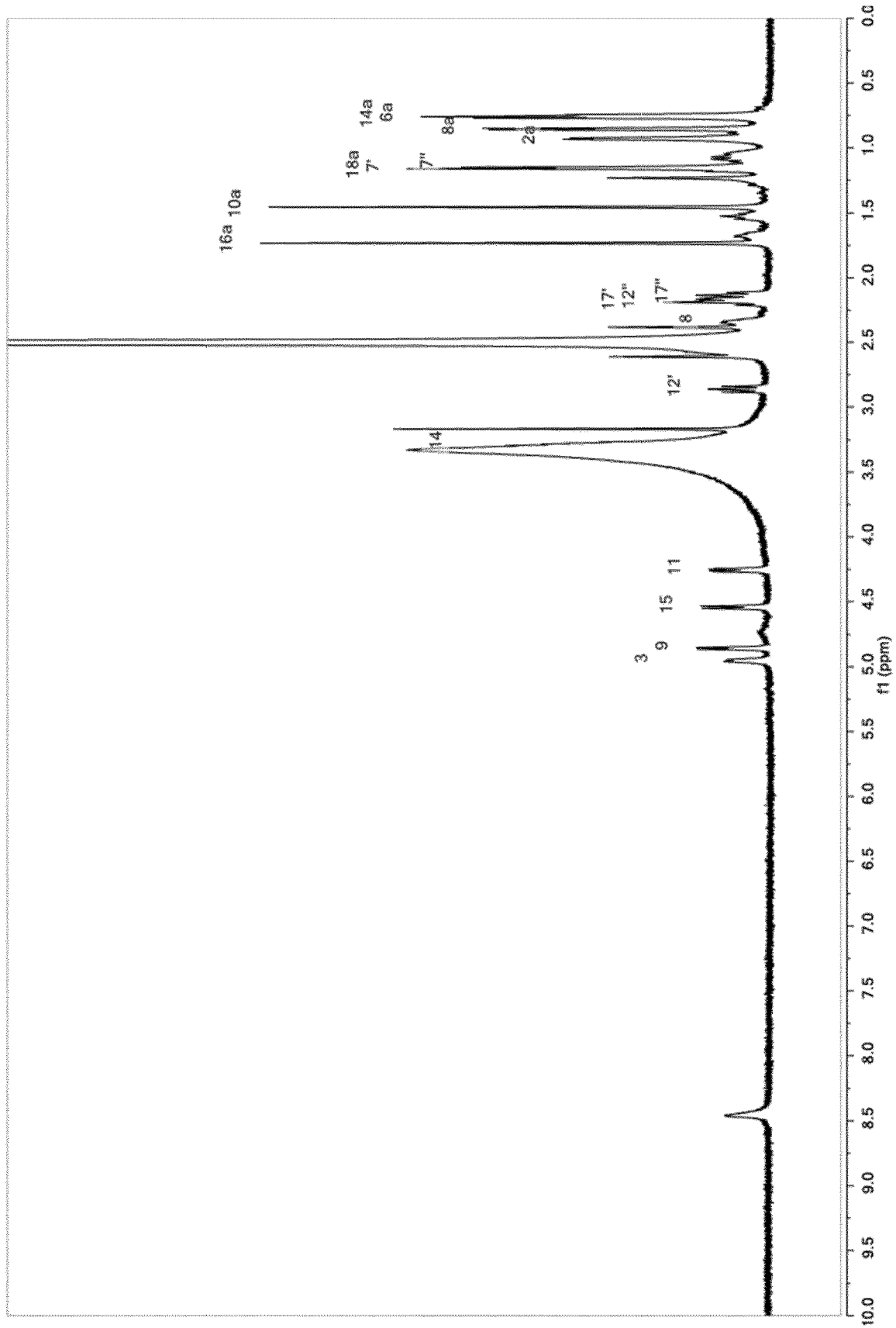
Figure 5I:
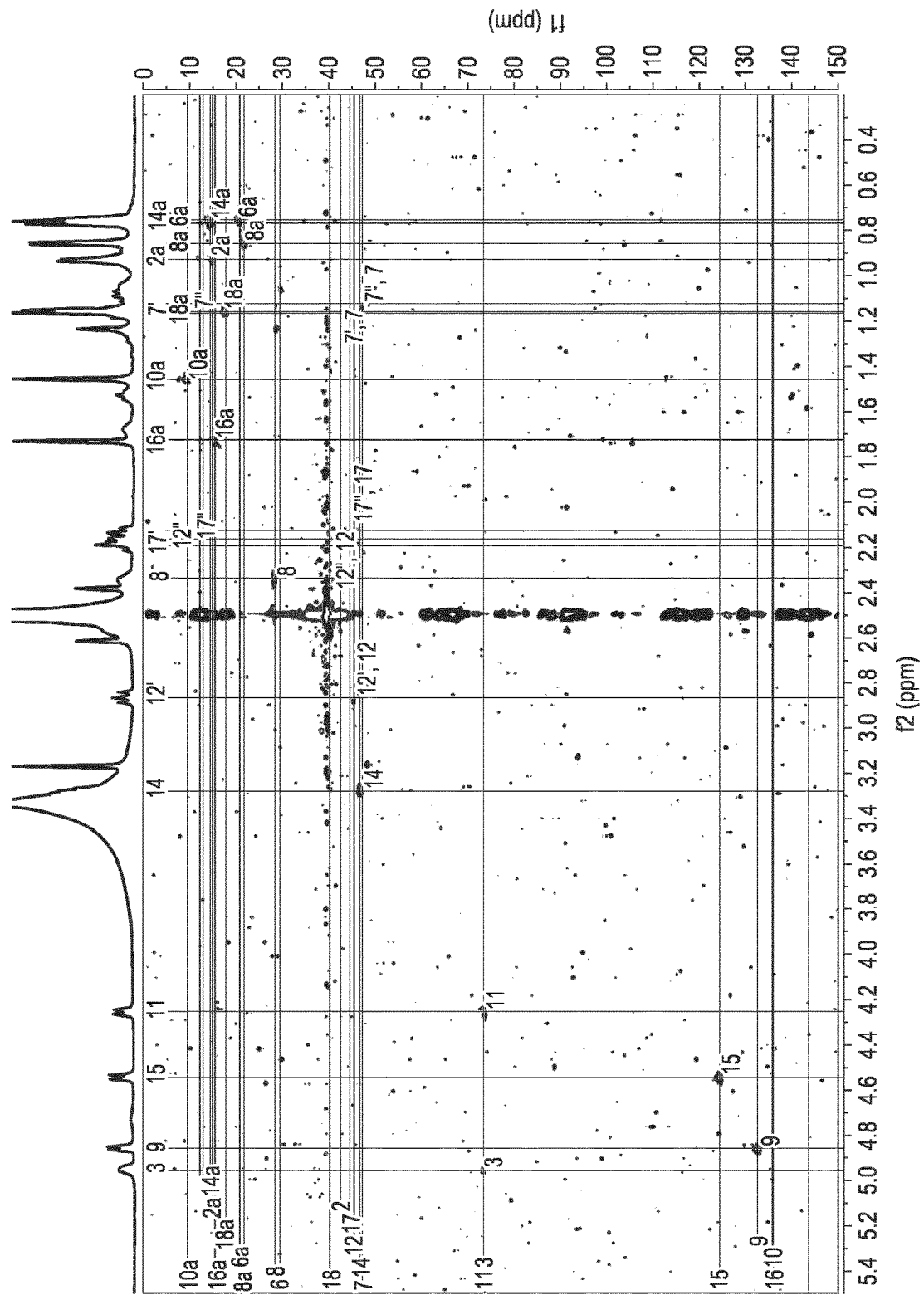

FIG. 5 shows 1D and 2D NMR data in deuterated chloroform (CDCl3) and/or deuterated DMSO (DMSO-$d_6$) of the unsaturated polyketide/macrocyclic lactone. A. $^1$H NMR spectrum of the unsaturated polyketide/macrocyclic lactone in CDCl$_3$ with 64 scans; B. Zoom of $^1$H NMR spectrum of the unsaturated polyketide/macrocyclic lactone in CDCl$_3$ with 16 scans; C. COSY NMR spectrum of the unsaturated polyketide/macrocyclic lactone in CDCl$_3$ with 8 scans; D. Edited-HSQC NMR spectrum of the unsaturated polyketide/macrocyclic lactone in CDCl$_3$ with 16 scans; E. HMBC NMR spectrum of the unsaturated polyketide/macrocyclic lactone in CDCl$_3$ with 64 scans; F. ROESY NMR spectrum of the unsaturated polyketide/macrocyclic lactone in CDCl$_3$ with 8 scans; G. HMBC NMR spectrum of the unsaturated polyketide/macrocyclic lactone in CDCl$_3$ with 64 scans; H. $^1$H NMR spectrum of the unsaturated polyketide/macrocyclic lactone in DMSO-$d_6$ with 64 scans; I. Edited-HSQC NMR spectrum of the unsaturated polyketide/macrocyclic lactone in DMSO-$d_6$ with 8 scans; J. HMBC NMR spectrum of the unsaturated polyketide/macrocyclic lactone in DMSO-$d_6$ with 256 scans.

The invention claimed is:

1. A method for treatment of a neurological disorder and/or improvement of memory function in an individual in need thereof, the method comprising administering to the subject a compound of general structural formula (Ia)

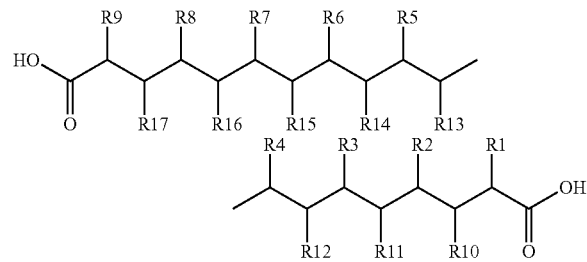

wherein R1 to R9 are individually selected from H and CH3; and
R10 to R17 are individually selected from H, C=O, and OH;
or a salt thereof, in an amount effective to promote lactate secretion in the individual,
the neurological disorder is selected from the group consisting of arachnid cysts, attention deficit/hyperactivity disorder (ADHD), autism, bipolar disorder, catalepsy, depression, encephalitis, epilepsy/seizures, infection, locked-in syndrome, meningitis, migraine, multiple sclerosis, myelopathy, Alzheimer's disease, Huntington's disease, Parkinson's disease, Tourette's syndrome, and combinations thereof.

2. The method of claim 1, wherein the compound is a macrolide.

3. The method of claim 1, wherein the compound is lactonised between the carboxylic acid group at position 19 and the alcoholic group at position 3, creating an 18 atom ring to form compound A:
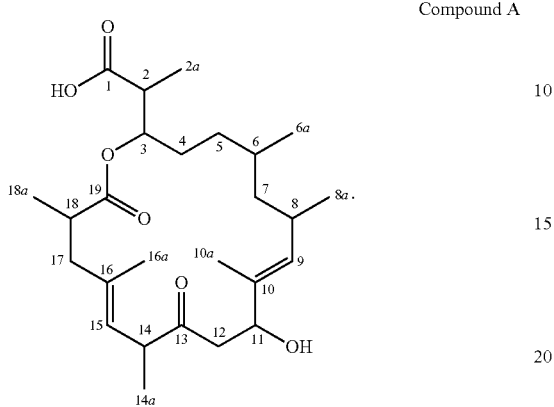
Compound A
* * * * *